(12) United States Patent
Wang et al.

(10) Patent No.: US 10,061,898 B2
(45) Date of Patent: Aug. 28, 2018

(54) AVATAR-BASED CHARTING METHOD AND SYSTEM FOR ASSISTED DIAGNOSIS

(71) Applicant: KAOHSIUNG MEDICAL UNIVERSITY, Kaohsiung (TW)

(72) Inventors: Cheng-Yuan Wang, Kaohsiung (TW); Ying-Fong Huang, Kaohsiung (TW); Jer-Chia Tsai, Kaohsiung (TW); Jer-Min Tsai, Kaohsiung (TW); Yu-Hsien Chiu, Kaohsiung (TW); I-Te Chen, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 889 days.

(21) Appl. No.: 14/478,527

(22) Filed: Sep. 5, 2014

(65) Prior Publication Data
US 2015/0261925 A1  Sep. 17, 2015

(30) Foreign Application Priority Data
Mar. 14, 2014  (TW) .............................. 103109379 A

(51) Int. Cl.
| | | |
|---|---|---|
| *G06F 19/00* | (2018.01) | |
| *G16H 10/60* | (2018.01) | |
| *G16H 50/20* | (2018.01) | |
| *G16H 15/00* | (2018.01) | |
| *G16H 50/50* | (2018.01) | |

(52) U.S. Cl.
CPC .......... *G06F 19/345* (2013.01); *G16H 10/60* (2018.01); *G16H 15/00* (2018.01); *G16H 50/20* (2018.01); *G06F 19/321* (2013.01); *G16H 50/50* (2018.01)

(58) Field of Classification Search
CPC ........ G06Q 50/22; G06Q 50/24; G06Q 40/08; G06Q 10/10; G06F 19/322; G06F 19/345; G06F 19/321; G16H 15/00; G16H 50/20; G16H 10/60; G16H 50/50
See application file for complete search history.

(56) References Cited

U.S. PATENT DOCUMENTS

| | | | |
|---|---|---|---|
| 8,458,610 B2 * | 6/2013 | Kenney ................ | G06F 19/322 715/705 |
| 2013/0110548 A1 * | 5/2013 | Kutty .................... | G06F 19/322 705/3 |
| 2013/0191160 A1 * | 7/2013 | Oran .................... | G06F 19/3437 705/3 |

* cited by examiner

*Primary Examiner* — Linh Giang Le
(74) *Attorney, Agent, or Firm* — Osha Liang LLP

(57) ABSTRACT

An avatar-based charting method for assisted diagnosis to improve the efficiency of medical practice. Through an anthropomorphic symptom record interface, the first page is the Genetic-Psycho-Social-Bio (GPSB) which assists in understanding the genetic, psychological, social-environmental, and biological characteristics of patients. A Subjective-Objective-Assessment-Plan (SOAP) diagnosis page aids in doctor diagnosis. A decision support diagnostic summary interface automatically generates the diagnosis summary and notifies of any unusual circumstances. Finally, a medical records module saves all information into a medical database in order to provide health care for subsequent tracking and evaluation.

3 Claims, 8 Drawing Sheets

AVATAR-BASED CHARTING METHOD AND SYSTEM FOR ASSISTED DIAGNOSIS

CROSS REFERENCE

The application claims priority of Taiwan Patent Application NO. 103109379, filed on Mar. 14, 2014, the content thereof is incorporated by reference herein.

BACKGROUND OF THE INVENTION

Field of the Invention

The present invention relates to computer-assisted diagnosis, and more specifically relates to an avatar-based charting system and method whereby users watch a perspective view with the aid of concept maps, which integrates the information of medical images, laboratory examination, patient self-reporting, and expert consultation.

Description of Related Art

Tremendous amounts of data are generated in daily medical practice. Based on this data, doctors make decisions about how to treat and care for a patient. Therefore, it would be better if the data could be integrated and more effectively presented to the doctors and other medical staff.

The original thrust to computerize the medical record came from Larry Weed's seminal work in 1969. The P.O.M.R. elevated each of the patient's problems to the highest level in the chart and then organized the S.O.A.P. format as the means of reporting how the problem was doing in the follow-up visits. He also championed the use of flow sheets to follow the data that accumulated around the problems for simpler analysis.

In medical practice, there are various kinds of data coming from different sources. Some of them, for example, blood pressure, pulse rate, body temperature and urine volume, are observed by nurses several times every day. Others like biochemical or serological tests are measured by a laboratory once a week, month, or even year. The ability to do in depth epidemiological studies requires the option to access a large number of records to withdraw and collate disease data. However, it is difficult to access large numbers of paper medical records that may be required to carry out epidemiological studies. The fact that the records are largely hand written or typed makes this type of data access a laborious non-automatable task.

Human factors exacerbate this irregularity. Sometimes a patient may be asked the same questions many times by doctors, nurses, medical students and nursing interns. There are considerable differences among doctors in the style of clinical testing and treatment of patients' problems. Clinical data may be easily missed by human error or a complicated hospital system.

Traditional medical education in the transfer of knowledge and skills uses static text and pictures in the document, or literature. Recently, the medical information network has gradually developed so that it brings the convenience of applications. Schmeling et al. (2011) uses a network Learning System to design an autopsy tests digital platform, simulating an autopsy situation to enhance the ability of post-mortem examination. Colsman et al. (2006) develops an immunological digital learning platform as a teaching utility. O'Neill et al. (2011) utilizes a digital learning platform to strengthen the knowledge and control of infection prevention in health care for medical students, so that these medical students have better learning results then other students. Marshall et al. (2011) assesses medical students with a digital learning platform for radiology workflow testing. As a result, these medical students achieve better results. McKenna et al. (2010) teaches medical students to identify patients with chronic facial features in a digital learning method; the results show that the diagnostic capabilities of medical students are enhanced.

Taiwan patent TW-201301075 discloses a knowledge management system for medical images and a method for generating the related knowledge. The knowledge management system establishes a knowledge database with integration of medical images and the related texts. However, it does not provide a logical relation between the content of the data.

In the knowledge management and digital content field, Taiwan patent TW-I257592 discloses an interactive digital learning system without description of logical interpretation. Even the application TW-201218066 discloses an interface configuration system for multiple display areas, which uses a processing apparatus to command an adjustment module to provide an adjustment scheme through optimization analysis, and the adjustment scheme includes a reconfiguration of the sizes or shapes of the display areas, resealing of the display contents, and displaying the display contents by scrolling or paging.

The conventional system described above provides, for example, an integrated information and communication platform for outcome and evidence-based medical research. Using the system, clinicians have difficulting in developing a logical interpretation of the medical education in physiology, pathology and systemic areas. Nowadays, medical education is in the infancy in utilizing digital textbooks, digital learning, electronic medical records and records of care delivery model to assist the diagnosis and clinical experience. Through the system, researchers may also collaborate with colleagues to validate and to refine the study and invite patients to participate in the study. Patients may further access the study through the system.

There are other occasions when medical personnel have more time to obtain detailed information from and about the patient, and/or the patient can provide additional information by themselves. In these circumstances, a detailed fully automated approach to developing a diagnosis is desired. There are yet other occasions when various combinations of the above are desired depending on the time and information available.

In view of the foregoing, a need exists in the art for a computer-assisted diagnosis with logical interpretation. In addition, a need exists for such an avatar-based charting system installed in a mobile device.

SUMMARY OF THE INVENTION

In general, an avatar-based charting system and method for assisted diagnosis is provided having various aspects addressed to overcome the shortcomings of the prior art as discussed above and provide certain other advantages. An objective of the present invention is to provide an avatar-based charting system to improve the efficiency of medical practice. Another objective of the present invention is to provide an avatar-based charting method comprising portable electronic devices to demonstrate feasibility.

In order to accomplish the above objectives and more, one embodiment of the avatar-based charting system comprises: a hardware processor and a non-transitory memory for executing applications and storing data of the avatar-based charting system, an anthropomorphic medical record interface, extracting a plurality of medical data from a patient medical informational source, and displaying Genetic-Psycho-Social-Bio (GPSB) information corresponding to a patient; a multi-level remote diagnosis module, generating pages displaying symptom of records with human organ graphics according to the Genetic-Psycho-Social-Bio (GPSB) information of the patient, simulating the inference procedure of the illness, which is a general and special health care mode of operation, wherein a doctor selects the patient and reads the GPSB page to observe genetics, psychology, sociology, biology information concerning the patient, identifying a patient's condition, then going to the Subjective-Objective-Assessment-Plan (SOAP) page with the human organ graphics for physical examination and diagnosis or impression; a decision support diagnostic summary interface, generating a diagnosis summary and providing at least an abnormal condition and review; a medical records module, modifying, adding, or saving the diagnosis summary into the patient medical informational source to provide parameters for subsequent tracking and evaluation.

In order to accomplish these objectives and more, another embodiment of the avatar-based charting method comprises: accessing a patient medical information database and reading a plurality of medical records concerning a specified patient; displaying an avatar showing transparent graphics of human organs; paging symptom of records with human organ graphics according to the medical records, combining an avatar for simulating the processes of inference to the patient's condition; showing the GPSB (Genetic-Psycho-Social-Bio) page to display genetic, psychotic, social-environmental, and biological characteristics of the patient; going to an SOAP (Subjective-Objective-Assessment-Plan) evaluating page to assist physical examination and diagnosis or impression; going to a decision support diagnostic summary interface, generating a diagnosis summary and providing at least an abnormal condition and review; and modifying, adding, or saving the diagnosis summary into the patient medical information database to provide data for subsequent tracking and evaluation.

Applying advancements in cognitive psychology, medical education, and electrical medical records, the invention provides an anthropomorphic medical information processes and auxiliary diagnosis system to improve the efficiency of medical practice. There are three main pages for displaying GPSB information, SOAP evaluation and diagnosis summary. The avatar-based charting system and method provides users with a perspective view with the aid of concept maps that integrate the information of medical images, laboratory examination, patient self-reporting, and expert consultation.

Therefore, the design of the avatar-based charting system for assisted diagnosis is non-obvious and sufficiently inventive, and reflects a same general patentability requirement. It is noted that the present invention has the advantages that the invention provides computer graphics and makes medical progress for the field.

BRIEF DESCRIPTION OF THE DRAWINGS

Embodiments of the invention will now be described, by way of example only, with reference to the accompanying drawings in which.

DETAILED DESCRIPTION OF THE INVENTION

The following description is merely exemplary in nature and is in no way intended to limit the present teachings, applications, or uses. Those of skill in the art will recognize that the following description is merely illustrative of the principles of the invention, which may be applied in various ways to provide many different alternative embodiments.

Figure 1:
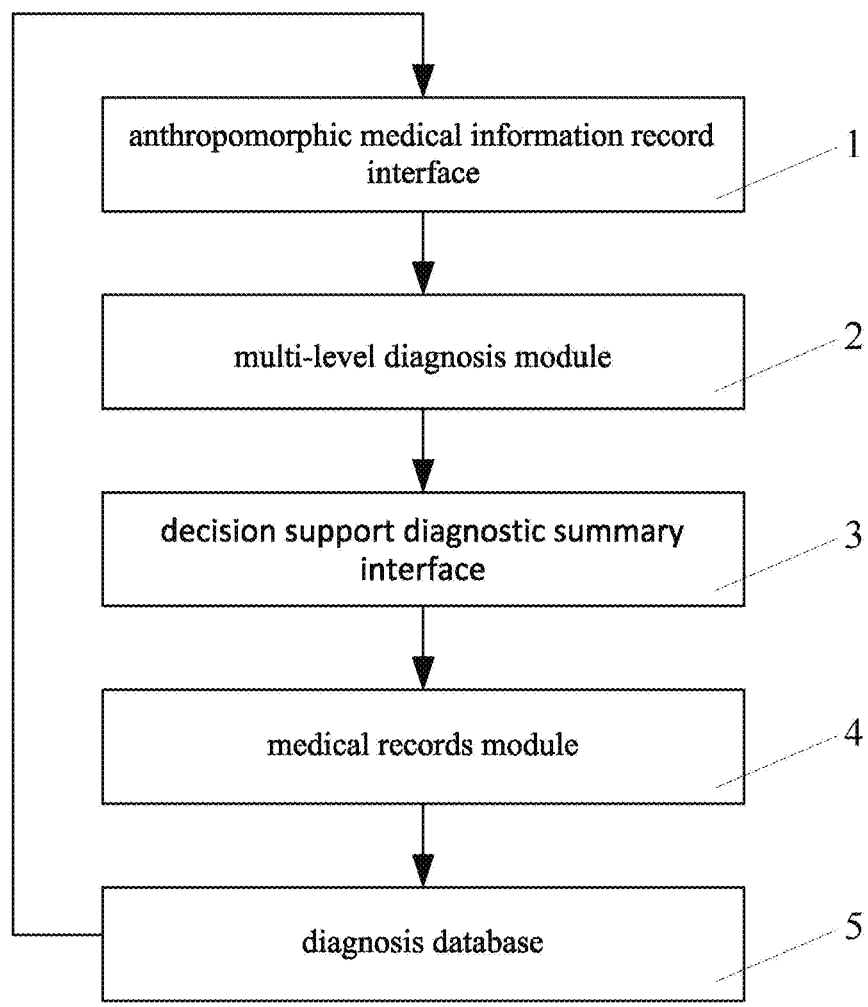
FIG. 1 is a schematic block diagram of the avatar-based charting system according to the present invention.

FIG. 1 depicts one embodiment of the schematic block diagram of the avatar-based charting system of the present invention, which comprises: an anthropomorphic medical information record interface 1, a multi-level diagnosis module 2, a decision support diagnostic summary interface 3, and a medical records module 4.

The anthropomorphic medical record interface 1 extracts medical data from a patient medical informational source, for example, a diagnosis database 5, and displays Genetic-Psycho-Social-Bio (GPSB) information corresponding to a patient. In other embodiments, GPSB information can be displayed on a projector, an electronic display or a mobile device. The multi-level remote diagnosis module 2 generates pages showing symptom records with computer graphics of human organs according to the Genetic-Psycho-Social-Bio (GPSB) information of the patient. The diagnosis module 2 is constructed with a multi-level mechanism for systematic diagnosis, which simulates the processes of the illness inference, wherein the logic of the processes is operation mode of general and special care. The user inputs a patient's name, a GPSB page is generated with genetics, psychology, sociology, biology information concerning the patient. After the patient's identification is checked, the SOAP (Subjective-Objective-Assessment-Plan) page is generated with the human organ graphics for physical examination and diagnosis or impression. A decision support diagnostic summary interface 3 generates a diagnosis summary and provides at least an abnormal condition and review. A medical records module 4 performs modifying, adding, or saving the diagnosis summary into the patient medical informational source 5 to provide data for subsequent tracking and evaluation. In one embodiment, the patient medical informational source 5 is connected to a medical information system on a local or remote database, for example, portable memory device, smart phone, tablet PC or cloud storage hard disk.

The avatar-based charting system of the present invention further comprises a hardware processor and a non-transitory memory for executing applications and storing data of the avatar-based charting system.

Figure 2:
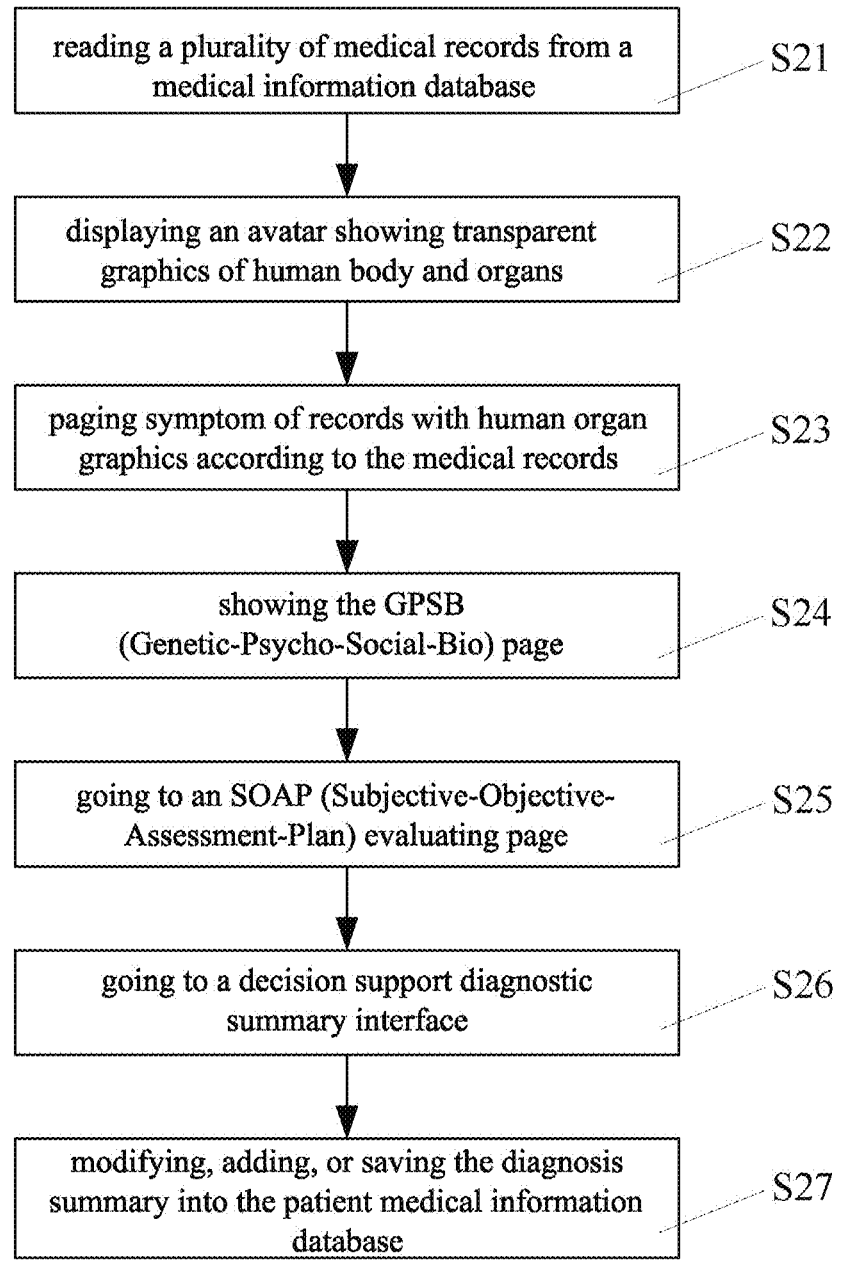
FIG. 2 is a flowchart of the avatar-based charting method according to the present invention.

FIG. 2 illustrates a flowchart of an avatar-based charting method for assisted diagnosis, which comprises: step S21 accessing a patient medical information database and reading a plurality of medical records concerning a specified patient; step S22 displaying an avatar showing transparent graphics of human body and organs; step S23 paging symptom of records with human organ graphics according to the medical records, combining an avatar for simulating the processes of inference to the patient's condition; step S24 showing the GPSB (Genetic-Psycho-Social-Bio) page to display genetic, psychological, social-environmental, and biological characteristics of the patient; step S25 going to an SOAP (Subjective-Objective-Assessment-Plan) evaluating page to assist physical examination and diagnosis or impression; step S26 going to a decision support diagnostic summary interface, generating a diagnosis summary and providing at least an abnormal condition and review; and step S27 modifying, adding, or saving the diagnosis summary into the patient medical information database to provide data for subsequent tracking and evaluation.

In the figures below, the pages in the Figures generated from the programs are multi-language compatible, thus English and Chinese characters are mixed in the content of page, for example, the XML page.

Figure 3:
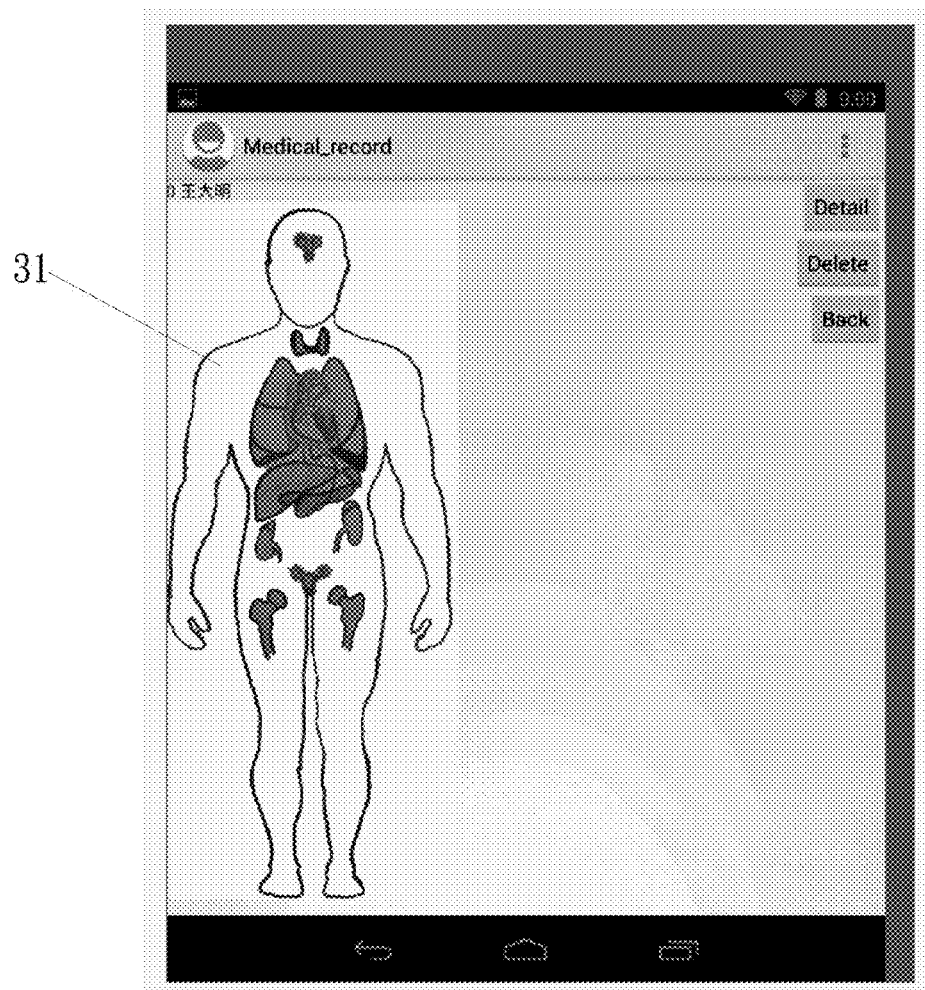
FIG. 3 is an illustrative page of the avatar-based charting system according to the present invention.

FIG. 3 is an illustrative page of the avatar-based charting system according to one embodiment, showing a transparent human body graphics 31 with organ parts including medical images and laboratory reports corresponding to pate, thoracic and abdominal organs, genitourinary system, skeletal system, which are displayed top to bottom, left to right on a screen.

Figure 4:
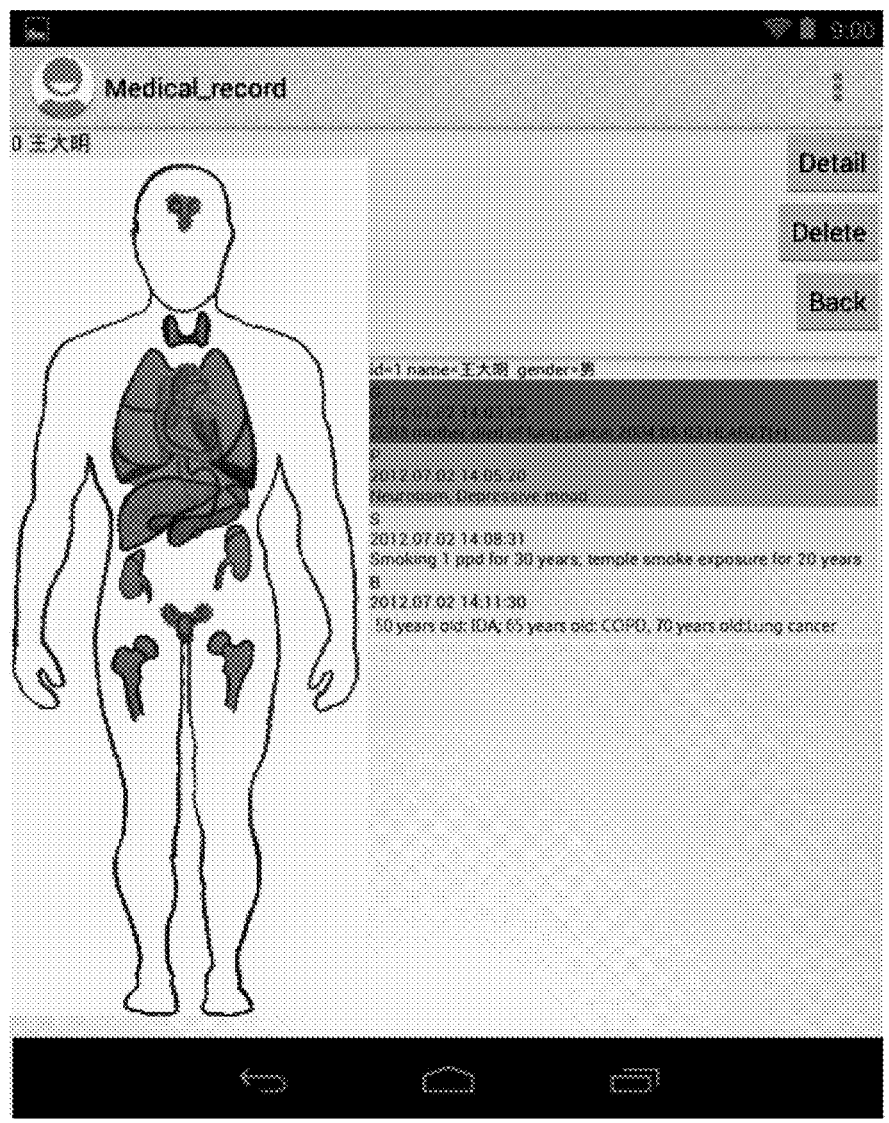
FIG. 4 is an illustrative page of GPSB according to the present invention.
Figure 5:
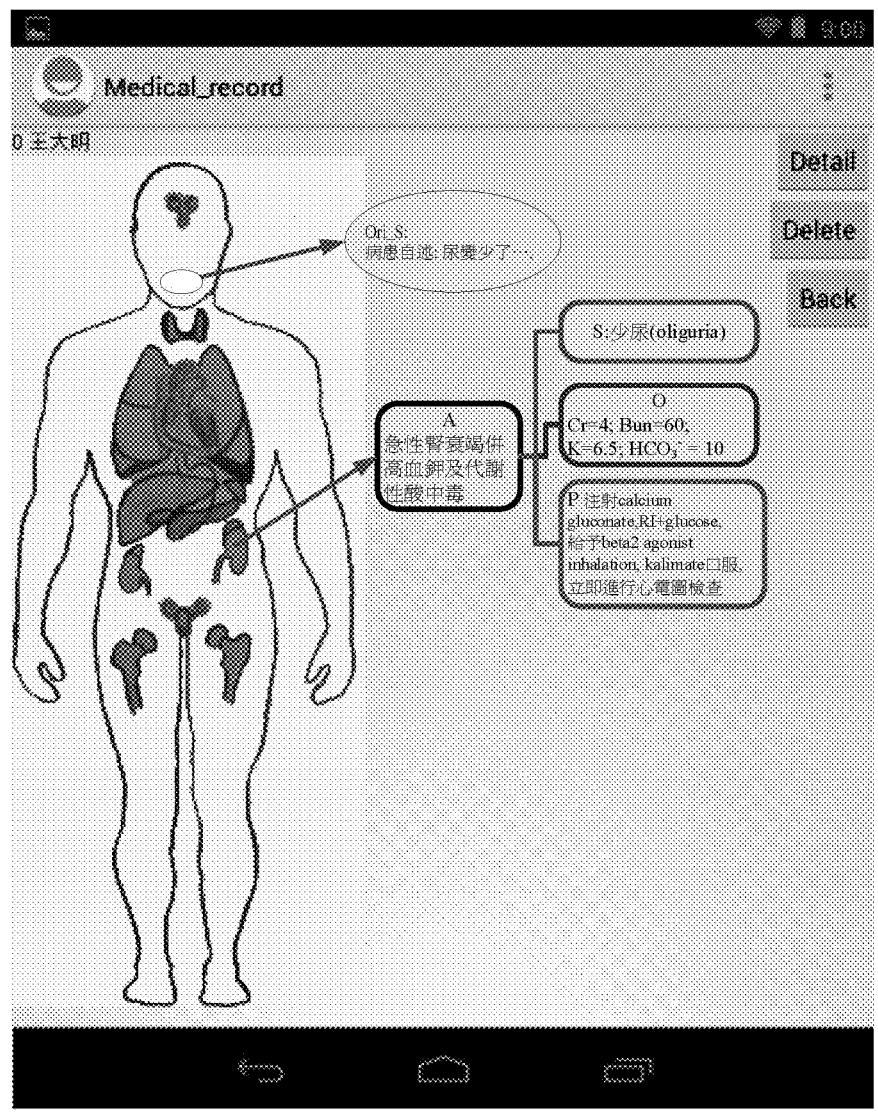
FIG. 5 is an illustrative page of SOAP according to the present invention.

FIG. 4 illustrates a GPSB page according to one embodiment, by which the doctor may identify the patient and understand the patient's chronology including genetic, psychological, social-environmental, and biological characteristics. Next, the SOAP page is executed and combined with the human organ graphics for physical examination and diagnosis or impression. Referring to FIG. 5, a decision support diagnostic summary interface generates a diagnosis summary and provides at least an abnormal condition and review. And finally, the medical records module is for modifying, adding, or saving the diagnosis summary into the patient medical informational source to provide data for subsequent tracking and evaluation. The patient medical informational source is connected to a medical information system on a local or remote database, and is selected from one of the group of a portable memory device, smart phone, tablet PC and cloud storage hard disk.

Furthermore, the SOAP (Subjective-Objective-Assessment-Plan) evaluation comprises automatically generating processes of auxiliary inference according to pages from standard operating procedures in the specific domain and related records thereof. The process of recording symptoms comprises speech recognition, handwriting recognition or gesture recognition.

The diagnosis summary further generates a set of quantification statistics, charts, or spreadsheet tables, which are displayed from top to down and left to right in a mix form, or played with animation and sound media effects.

According to the requirements of specialized clinicians the present invention provides a multi-level mechanism for systematic diagnosis, and solution to the health care procedures and related single record thereof. The medical records are collected and induced from routine examinations, clinical pathways, cases, systematic reviews and clinical reasoning diagnosis comprising medical records, properties, categories and diagnostic procedure results. A virtual figure shows some parts of the human body and organs in an abstract way, that may be displayed in HTML or XML form thereby simplifying diagnostic procedures and record symptoms. Further, the clinical care professionals can read a systematic integration of information for interpretation assistance.

Accordingly, the SOAP (Subjective-Objective-Assessment-Plan) evaluation comprises automatically generating processes of auxiliary inference according to pages from standard operating procedures in a specific medical domain and related records thereof.

By collecting the related medical records on the pages and rendering anthropomorphically, all diagnostic processes become multi-page views and records programs. Clinicians set their own requirements or characteristics according to their specialty view page, and record the project with logic steps of the program. The charting system comprising this programming executes the multi-step mechanism to generate pages on a projector, an electronic display or a mobile device. Also, automatic pagination generates the symptoms pages to simulate the process steps of illness inference. The symptoms recording comprises handwriting, speech recognition or gesture recognition, the operation performed using tap indicators, acoustic control, touch control and gesture control or software functions.

Figure 6:
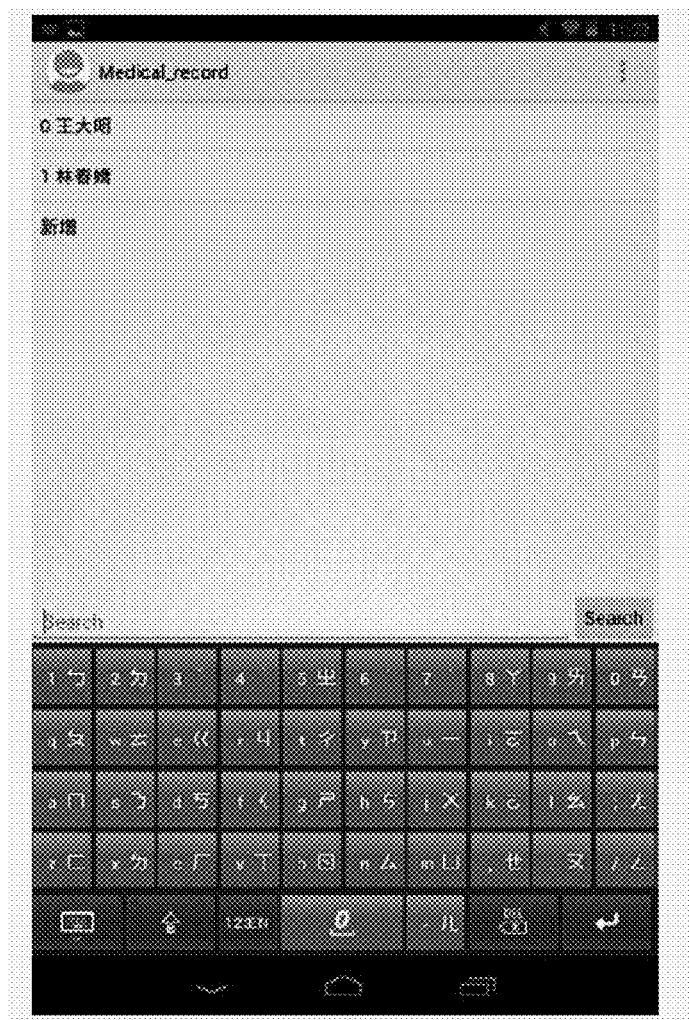
FIG. 6 illustrates a patient selection page according to the present invention.
Figure 7:
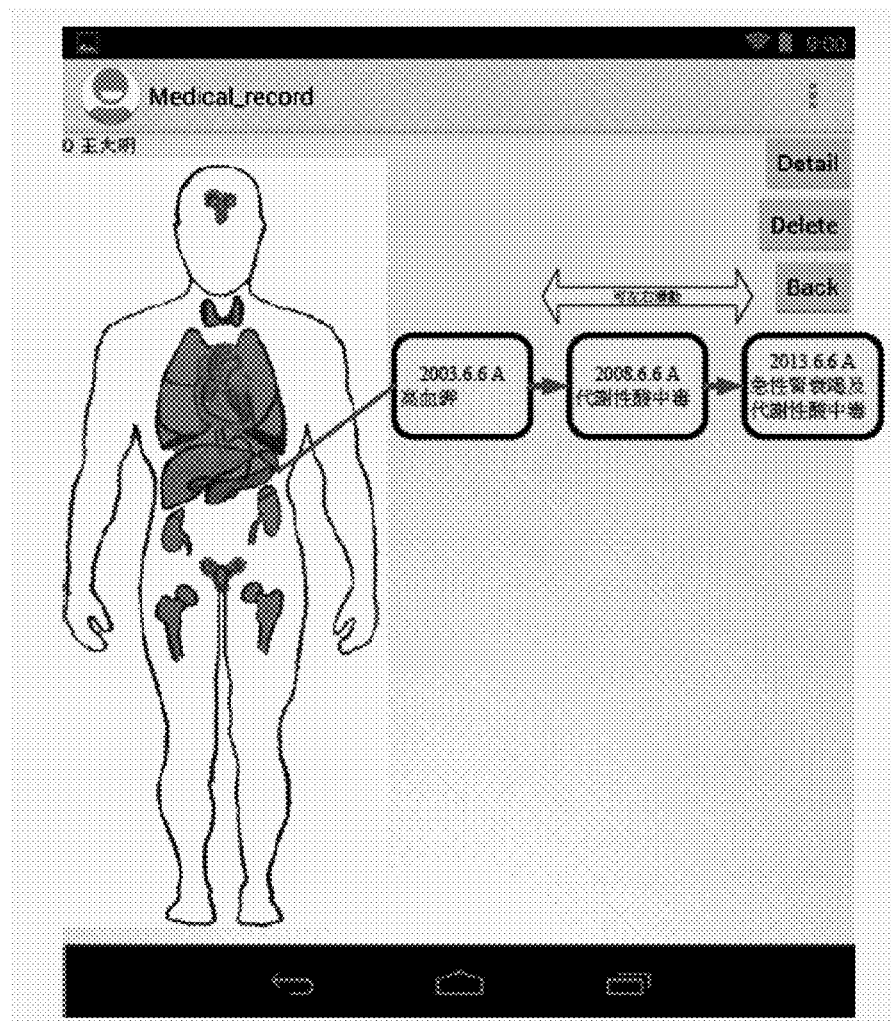
FIG. 7 is an illustrative page of GPSB according to the present invention.
Figure 8:
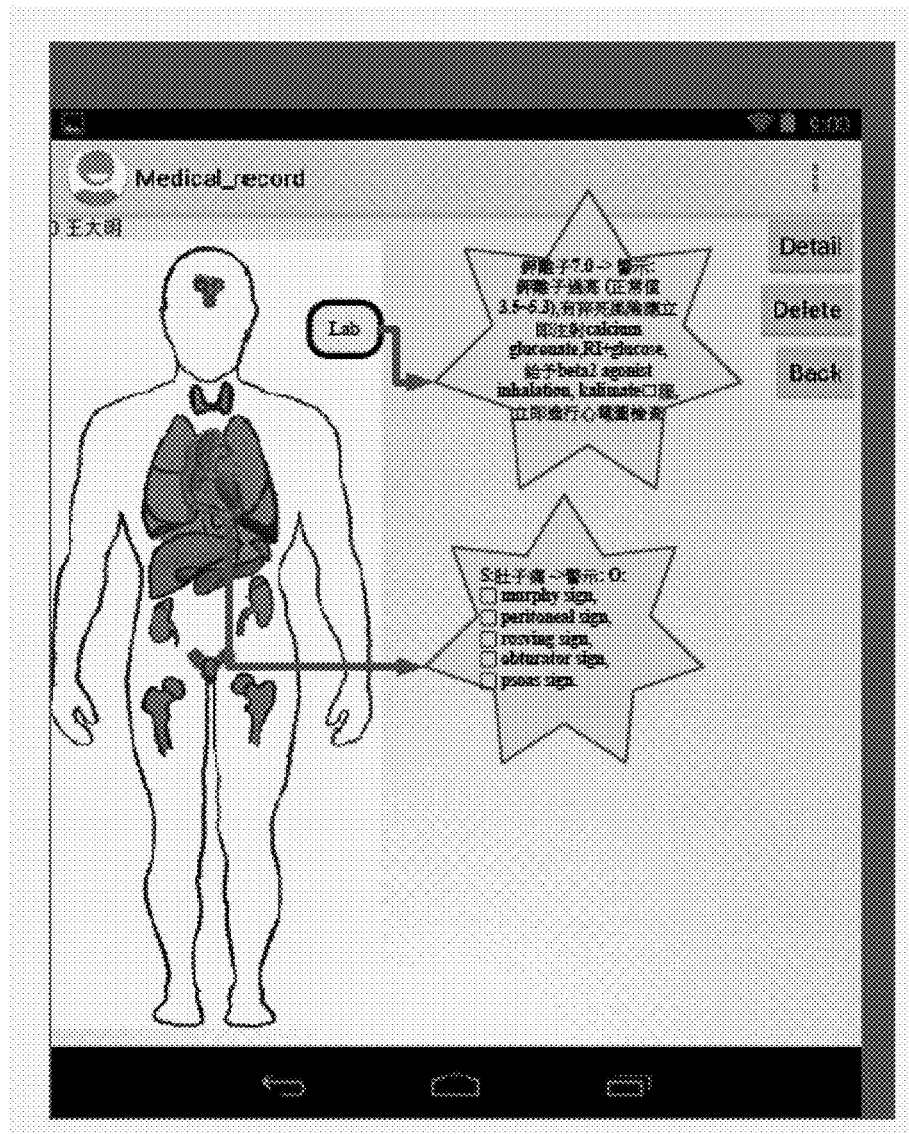
FIG. 8 illustrates an warning window of the medical record according to the present invention.

In one embodiment, the invention is applied with General Internal Medicine, the charting system based on the Android system with SQLite database has three main home pages comprising a GPSB page, a SOAP page and a decision support diagnostic summary page running on a tablet computer. FIG. 6 illustrates a patient selection page. When a doctor enters the charting system, a log-in page pops-up for selecting a patient's name. Next, the GPSB page is displayed with the patient's picture, shown in FIG. 7, after the patient's medical records are found. The data of the patient's medical records are arranged in time series, the earlier event is on the left most side, and the picture can identify the patient with certainty.

By the integration of medical records, after understanding the genetic, psychological, family medical history of patients, the SOAP page is displayed in FIG. 5. Subjective and objective examination, diagnosis and prescription information about the patient are displayed from top to bottom, left to right corresponding to the figure and organ parts. The abnormal situation has red color marking(s) or a warning description for supporting decision making. Furthermore, clicking on the red part or warning description, in one embodiment the related information and diagnosis are shown as in the list below:

Lab:
potassium ion 7.0→Warning: potassium ion is high (normal value 3.5~5.3)' risk of sudden death and inject calcium gluconate, RI+glucose, beta2 agonist inhalation, kalimate oral, immediately an electrocardiograph examination.

S: stomachaches→Warning: O: select check box
murphy sign,
peritoneal sign,
rosving sign,
obturator sign,
psoas sign.

Via an anthropomorphic symptom record interface, medical personnel and patients can see through important parts of the human body and organs. And the multi-level mechanism for systematic diagnosis can automatically produce symptoms record page and display along with the Anthropomorphic symptom record interface. In addition, the first page is the Genetic-Psycho-Social-Bio (GPSB) which allows understanding of the genetic, psychological, social-environmental, and biological characteristics of patients. The Subjective-Objective-Assessment-Plan (SOAP) diagnosis page helps in doctor diagnosis. The Decision Support Diagnostic Summary Interface automatically generates the diagnosis summary and notifies of unusual circumstances. Finally, the Medical records module stores all information into a medical database in order to provide health care for subsequent tracking and evaluation.

The invention is non-obvious and sufficiently inventive, and reflects a same general patentability requirement. It is noted that the present invention has the advantages that the invention provides computer graphics for assisted diagnosis and makes practical progress on the field.

While the invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. An avatar-based charting system for assisted diagnosis, comprising:
    a hardware processor and a non-transitory memory for executing applications and storing data of the avatar-based charting system;
    an anthropomorphic medical record interface comprising a first portion of the applications and configured to
        extract a plurality of medical data from a patient medical informational source, and
        display Genetic-Psycho-Social-Bio (GPSB) information corresponding to a patient;
    a multi-level remote diagnosis module comprising a second portion of the applications and configured to
        generate pages displaying symptom of records with human organ graphics according to the Genetic-Psycho-Social-Bio (GPSB) information of the patient,
        simulate the inference procedure of the illness, wherein a doctor selects the patient and observes the GPSB page to gain an understanding of genetics, psychological, sociological, and biological information concerning the patient,
        identify patient's condition, then accessing a Subjective-Objective-Assessment-Plan (SOAP) page with human organ graphics for physical examination and diagnosis, and
        generating processes of auxiliary inference according to pages from standard operating procedures in a specific medical domain and related records thereof with reference to the human organ graphics in the SOAP page;
    a decision support diagnostic summary interface comprising a third portion of the applications and configured to generate a diagnosis summary and providing at least an abnormal condition and noticing of unusual circumstances for review; and
    a medical records module comprising a fourth portion of the applications and configured to modify, add, or save the diagnosis summary into the patient medical informational source for subsequent tracking and evaluation,
    wherein the anthropomorphic medical records are displayed on a projector, an electronic display or a mobile device, and
    wherein the patient medical informational source is connected to a medical information system on a local or remote database and comprises a portable memory device, smart phone, tablet PC or cloud storage hard disk.

2. The avatar-based charting system as claimed in claim 1, wherein the human organ graphics is a transparent human body graphics comprising medical images and laboratory reports corresponding to pate, thoracic and abdominal organs, genitourinary system, skeletal system, which are displayed from top to bottom, left to right on a screen.

3. The avatar-based charting system as claimed in claim 1, wherein the diagnosis summary is a set of medical statistics, charts, or a spreadsheet table, which are displayed from top to bottom, left to right in a mixed form, or combined with animation and sound.

* * * * *